United States Patent
Wang et al.

(10) Patent No.: US 8,116,509 B2
(45) Date of Patent: Feb. 14, 2012

(54) ELECTROMAGNETIC ULTRASONIC TRANSDUCER AND ARRAY THEREOF

(75) Inventors: Hai Wang, Chongqing (CN); Siyuan Yan, Chongqing (CN); Li Jing, Chongqing (CN); Aihua Mao, Chongqing (CN)

(73) Assignee: Chongqing Ronghai Medical Ultrasound Industry Ltd., Chongqing (CN)

( * ) Notice: Subject to any disclaimer, the term of this patent is extended or adjusted under 35 U.S.C. 154(b) by 365 days.

(21) Appl. No.: 12/519,469

(22) PCT Filed: Feb. 14, 2007

(86) PCT No.: PCT/CN2007/000539
§ 371 (c)(1), (2), (4) Date: Jun. 16, 2009

(87) PCT Pub. No.: WO2008/074200
PCT Pub. Date: Jun. 26, 2008

(65) Prior Publication Data
US 2010/0018315 A1    Jan. 28, 2010

(30) Foreign Application Priority Data

Dec. 19, 2006  (CN) .......................... 2006 1 0167720

(51) Int. Cl.
*H04R 1/00* (2006.01)
*H04R 9/06* (2006.01)
*H04R 11/02* (2006.01)

(52) U.S. Cl. ...................................... 381/396; 381/400
(58) Field of Classification Search .................. 381/396, 381/398, 408, 412, 414, 417–420, 431
See application file for complete search history.

(56) References Cited

U.S. PATENT DOCUMENTS

| 4,777,824 A | 10/1988 | Alers et al. |
| 6,671,383 B2 | 12/2003 | Usuki et al. |

FOREIGN PATENT DOCUMENTS

| CN | 1253463 A | 5/2000 |
| JP | 59-160757 A | 9/1984 |
| JP | 2003-319493 A | 11/2003 |

*Primary Examiner* — Tuan Nguyen
(74) *Attorney, Agent, or Firm* — The Webb Law Firm (57) ABSTRACT

An electromagnetic ultrasonic transducer and an array thereof are provided. This electromagnetic ultrasonic transducer includes a support, an elastic board disposed on the support, a magnetizer on the elastic board, and a magnet field generator for vibrating the magnetizer, wherein, the thickness of the magnetizer is of the order of microns. The thickness of the elastic board is also of the order of microns. This electromagnetic ultrasonic transducer is able to produce acoustic waves of high frequency, which are useful for ultrasonic therapy.

30 Claims, 8 Drawing Sheets

ELECTROMAGNETIC ULTRASONIC TRANSDUCER AND ARRAY THEREOF

FIELD OF THE INVENTION

The present invention pertains to the field of ultrasonic therapy, and relates to ultrasonic transducer for ultrasonic therapy and, particularly to an electromagnetic ultrasonic transducer and an array thereof.

BACKGROUND OF THE INVENTION

The electromagnetic ultrasonic transducer is a new type of ultrasonic waves source and it mainly comprises elastic vibration slice, vibrating coil (or magnet conducting vibrating diaphragm) and magnetostatic coil (or permanent magnet). Its working principle is as follows: an electrified coil is affected by Lorentz Force in a magnetic field. When alternating current goes through the coil, the bulk and direction of force on the vibrating coil will vary accordingly. If the vibrating coil is fixed on the elastic vibration slice, the Lorentz Force on the vibrating coil makes the elastic vibration slice vibrate and accordingly the sound waves are transmitted therefrom. The electromagnetic horn is made by use of this principle.

Because the electromagnetic ultrasonic transducer has advantages of no contact with the surface of medium material, no need to apply acoustic coupling agent, good repeatability, high speed for detection, etc., it is widely employed in the field of nondestructive examinations. But the electromagnetic ultrasonic transducer used in ultrasonic examinations has a low frequency and the focusing is hard to be realized, thus, this kind of electromagnetic ultrasonic transducer for inspections cannot be applied to ultrasonic therapy directly.

SUMMARY OF THE INVENTION

Aiming at the disadvantages of the prior art as mentioned above, the technical solutions of the present invention are to provide an electromagnetic ultrasonic transducer and an array thereof, which can produce high-frequency sound wave and can be used for ultrasonic therapy. This array can be grouped randomly and can be formed in any shape and can flexibly control a plurality of ultrasonic transducer array elements.

The technical solutions for the problems proposed by the present invention are as follows: this electromagnetic ultrasonic transducer comprises an elastic board disposed on a support, a magnetizer on the elastic board and a magnet field generator for making the magnetizer vibrate. Wherein, the thickness of magnetizer is of the order of microns.

In prior art, the size of elastic coil or elastic magnet conducting diaphragm is generally of the order of centimeter. The frequency of this kind of ultrasonic transducers is mostly within the range of audio frequency. The smaller the size of elastic coil or elastic magnet conducting diaphragm, the higher the generated frequency of ultrasonic waves, and the maximum generated frequency of ultrasonic waves can reach megahertz level. Therefore, the magnetizer can be made as one of the order of microns in the present invention by use of micromachining technology and accordingly the elastic coil or elastic magnet conducting diaphragm can produce ultrasonic waves with high-frequency.

When the elastic magnet conducting diaphragm is used for magnetizer, preferably, its thickness shall range from 1.0 to 300 microns.

Preferably, the thickness of said elastic board is also of the order of microns. When the elastic board is rectangle-shaped, preferably, its length and width range from 10 to 1000 microns and its thickness ranges from 5 to 500 microns. When the elastic board is round-shaped, preferably, its diameter ranges from 10 to 1000 microns and its thickness ranges from 5 to 500 microns. Accordingly, the elastic board and the elastic magnet conducting diaphragm on it can be formed as a whole. The smaller the size of elastic board, the higher its resonance frequency, therefore, when the size of elastic board is also of the order of microns, the frequency of ultrasonic transducer can be more than megahertz level.

Preferably, the support adopts soft magnet. Said magnet field generator may include a support made of soft magnet, coils wound on this soft magnet and A. C. power supply connected to the coils.

More preferably, the winding direction of coils on the support makes the direction of inductive current generated in the elastic magnet conducting diaphragm be vertical to the direction of magnetic field in the soft magnet. At this time, the Lorentz Force generated in the magnet field generator is the maximum and the magnetic attraction to the magnetizer is also the maximum. Under the action of this force, the elastic board can generate the maximum vibration and transmit ultrasound waves with extremely high frequency.

More preferably, the shape of said support may be a concave one. Two ends of the elastic board are fixed on two protuberant parts at both ends of the support by elastic fixing material. Thus, an air sink is formed at the concave in the middle of the support. The concave soft magnet is easy and convenient to generate the magnetic field parallel to the winding direction of coils and accordingly the maximum Lorentz Force is generated to attract the magnetizer. The air sink formed at the concave in the middle of the concave support is a favorable condition for the elastic unit (referring to the elastic board and the magnetizer on it) to generate vibration and meanwhile, it is a favorable condition for the elastic unit to transmit ultrasonic waves because of small damping but big ultrasonic attenuation of the air sink.

In the present invention, other shapes, such as C-shape and E-shape may be adopted for the support. But the concave support is the preferable one because it is processed simply and has a low manufacturing cost.

In order to ensure the intensity of ultrasonic waves generated by the elastic unit as high as possible, preferably, the current frequency of said A. C. power supply connected to the coils is equal to the resonance frequency of the air sink. This frequency is more than 0.1 MHz and the best frequency shall be more than 0.5 MHz. Because the resonance frequency of the air sink depends on the physical size of the air sink, preferably, the length of air sink ranges from 10 to 200 microns, the width from 10 to 200 microns and the thickness from 10 to 50 microns.

When the elastic coil is used for magnetizer, preferably, the diameter of the coil ranges from 0.5 to 100 microns and the thickness ranges from 0.5 to 200 microns.

The elastic coil may adopt photolithographic coil. By use of semiconductor photolithography and chemical corrosion technology, the elastic coil can be manufactured as the photolithographic coil of the order of microns.

The support may use non-magnetizable material. The magnet field generator adopts the soft magnet wound by coils. The coils are connected to a D.C. power supply and the photolithographic coils are connected to an A. C. power supply.

The shape of said soft magnet may be concave. The support is fixed at the concave in the middle of soft magnet. The coils wound around two protuberant parts at the ends of the soft magnet.

The magnet field generator may also use permanent magnet. Said photolithographic coils are connected to an A. C. power supply. Said permanent magnet is concave-shaped. The support is fixed at the concave in the middle of the permanent magnet.

When the magnet field generator uses permanent magnet, the support may be disposed on the permanent magnet and connected to it. Said photolithographic coils are connected to an A. C. power supply. Wherein, the permanent magnet may be replaced by the soft magnet wound by coils and the coils are connected to a D.C. power supply.

More preferably, the winding direction of coils on the soft magnet makes the direction of current in the photolithographic coils be vertical to the direction of magnetic field in the soft magnet. At this time, the Lorentz Force generated in the magnet field generator is the maximum and the magnetic attraction to the magnetizer is also the maximum. Under the action of this force, the elastic board can generate the maximum vibration and transmit ultrasonic waves with extremely high frequency.

More preferably, the shape of said support may be a concave one. Two ends of the elastic board are fixed on two protuberant parts at both ends of the support by elastic fixing material. Thus, an air sink is formed at the concave in the middle of the support. The concave soft magnet is easy and convenient to generate the magnetic field parallel to the winding direction of coils and accordingly the maximum Lorentz Force can be generated to attract the magnetizer. The air sink formed at the concave in the middle of the concave support is a favorable condition for the elastic unit to generate vibration and meanwhile, it is also a favorable condition for the elastic unit to transmit ultrasonic waves because of small damping but big ultrasonic attenuation of the air sink. Other shapes, such as C-shape and E-shape may be adopted for the support. But the concave support is the preferable one because it is processed simply and has a low manufacturing cost.

In an electromagnetic ultrasonic transducer, the support uses non-magnetizable material. The magnetizer is disposed under the support and it adopts the soft magnet wound by coils. The coils are connected to a D.C. power supply and said photolithographic coils are connected to an A. C. power supply. For an array of electromagnetic ultrasonic transducers including the electromagnetic ultrasonic transducers as mentioned above, the thickness of the elastic board in each ultrasonic transducer is of the order of microns; all the supports are integrated; all the magnet field generators in the ultrasonic transducers are integrated and are connected to a D.C. power supply; the photolithographic coils are connected to each other in parallel and then connected to an A. C. power supply. Alternatively, for an array of electromagnetic ultrasonic transducers including the electromagnetic ultrasonic transducers as mentioned above, the thickness of the elastic board in each ultrasonic transducer is of the order of microns; all the supports are integrated; the soft magnets wound by coils are respectively fixed under every elastic board; the photolithographic coils are connected to each other in parallel and then connected to an A. C. power supply.

In an electromagnetic ultrasonic transducer, the support uses non-magnetizable material. The magnet field generator adopts the permanent magnet. The support is disposed on the permanent magnet and is connected to it by a fixed joint. Said photolithographic coils are connected to an A. C. power supply. For an array of electromagnetic ultrasonic transducers including the electromagnetic ultrasonic transducers as mentioned above, the thickness of the elastic board in each acoustic transducer is of the order of microns; all the supports are integrated, the photolithographic coils are connected to each other in parallel and then connected to an A. C. power supply.

Because the electromagnetic ultrasonic transducer has its own unique advantages, for example, strong power generated by it and relatively simple manufacturing process, the electromagnetic ultrasonic transducers array of the present invention, as a complete electromagnetic ultrasonic transducer, is formed by a plenty of small electromagnetic ultrasonic transducers of the order of microns, while the complete electromagnetic ultrasonic transducer is not assembled directly with traditional large-sized components. The frequency of the complete electromagnetic ultrasonic transducer is basically determined by the frequency of each small transducer unit. Therefore, this improvement on structure can greatly increase the frequency of the electromagnetic ultrasonic transducer.

Wherein: 1—Soft magnet 2—Coil 3—A.C. power supply 4—D.C. power supply 5—Elastic fixing material 6—Elastic board 7—Magnetic conducting diaphragm 8—Support 9—Permanent magnet 10—Air sink 11—Comb permanent magnet 12—Fixing for comb permanent magnet 13—Comb soft magnet 14—Photolithographic coil 15—Fixing for comb soft magnet

DETAILED DESCRIPTION OF PREFERRED EMBODIMENTS

The present invention will be further explained below in detail with reference to the preferred embodiments and accompanying drawings.

The following embodiments are the non-restrictive embodiments of the present invention.

Embodiment 1

Figure 1:
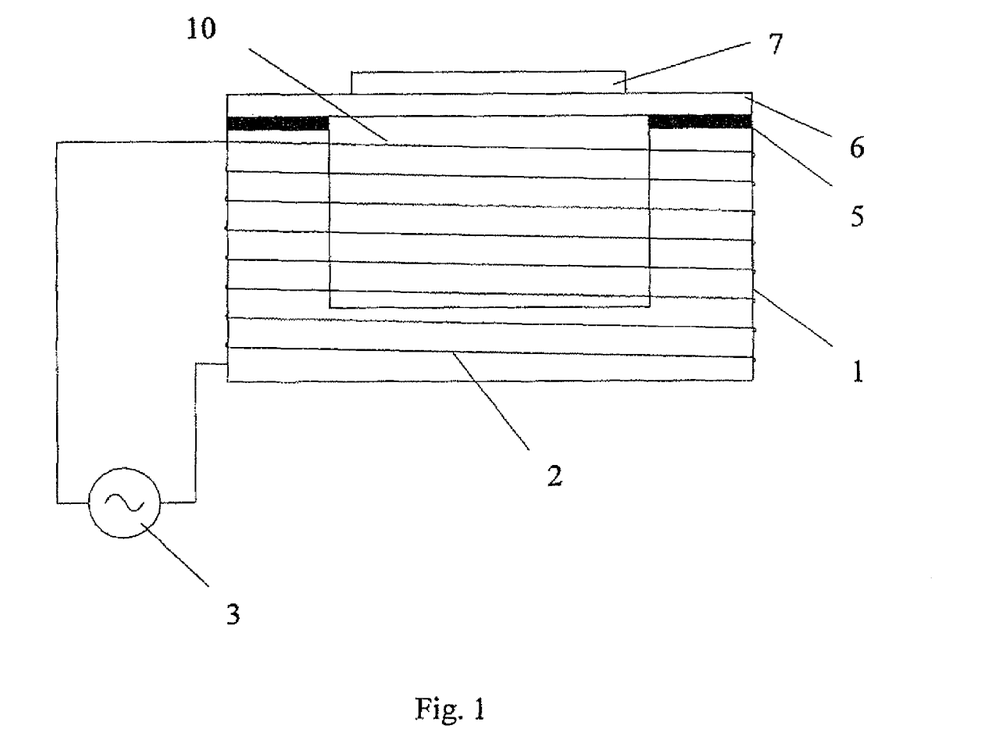
FIG. 1 is a structural diagram of electromagnetic ultrasonic transducer of the embodiment 1 of the present invention.

As shown in FIG. 1, the electromagnetic ultrasonic transducer comprises: an elastic board 6, a magnetizer on the elastic board 6 and a magnet field generator for making the magnetizer vibrate. Wherein, the magnetizer is of the order of microns and it is plated on the elastic board 6. The magnetizer adopts magnet conducting diaphragm 7, for example, nickel, with a thickness ranging from 0.1 to 100 microns. In this embodiment, the magnet field generator comprises: a support 8 made of soft magnet for supporting elastic board 6, coil 2 wound on this soft magnet and A. C. power supply 3 connected to the coil 2.

In this embodiment, the elastic board 6 also adopts a rectangle-shaped plate of the order of microns with a length ranging from 10 to 300 microns, a width ranging from 10 to 300 microns and a thickness ranging from 5 to 500 microns. Because the elastic board 6 has a high elasticity, good process ability and good mechanical strength, it can be made by the metal material, such as spring steel, glass, ceramics, etc.

In order to ensure the space for vibrating when the elastic board 6 vibrates, the support 8 and the elastic board 6 are jointed by elastic fixing material 5. The elastic fixing material 5 may be made by soft material, like silica gel. The soft magnet 1 is a concave one. Two ends of the elastic board 6 are fixed on two protuberant parts at both ends of the support 8 by elastic fixing material 5. Thus, an air sink 10 is formed at the concave in the middle of the support 8. In this embodiment, the length of the air sink 10 ranges from 10 to 200 microns, the width from 10 to 200 microns and the thickness from 10 to 50 microns.

Because different ultrasonic parameters (for example, frequency) are needed for treatment of different diseases and different elastic boards can be selected to gain different ultrasonic frequencies, the elastic board 6 may be made in any shape to meet the requirements of different diseases. When the skin diseases are treated, the board can be a flat one. When some solid tumors are treated, the board can be a spherical one, single arc surfaced one, etc.

In order to ensure the intensity of ultrasonic waves generated by the elastic unit as high as possible, preferably, the current frequency of said A. C. power supply 3 is equal to the resonance frequency of the air sink. At least, this frequency shall be more than 0.1 MHz and the best frequency shall be more than 0.5 MHz. The frequency of 5 MHz is used in this embodiment.

In order to generate the maximum Lorentz Force, the winding direction of the coil 2 on the support makes the direction of inductive current generated in the elastic magnet conducting diaphragm 7 be vertical to the direction of magnetic field in the soft magnet.

When this electromagnetic ultrasonic transducer is used, the A. C. power supply 3 provides A. C. power to the coil 2. Because the coil 2 winds around the support 8 made from the soft magnet, the soft magnet is magnetized when the power goes through the coil. Under the action of A. C. power supply, the magnetic field intensity of the soft magnet varies according to the A. C. power supply and accordingly the attraction to the magnet conducting diaphragm 7 also varies. Because the soft magnet is fixed and the elastic board 6 is movable, this attraction makes the elastic board 6 vibrate continuously and generate the ultrasonic waves.

Embodiment 2

Figure 2:
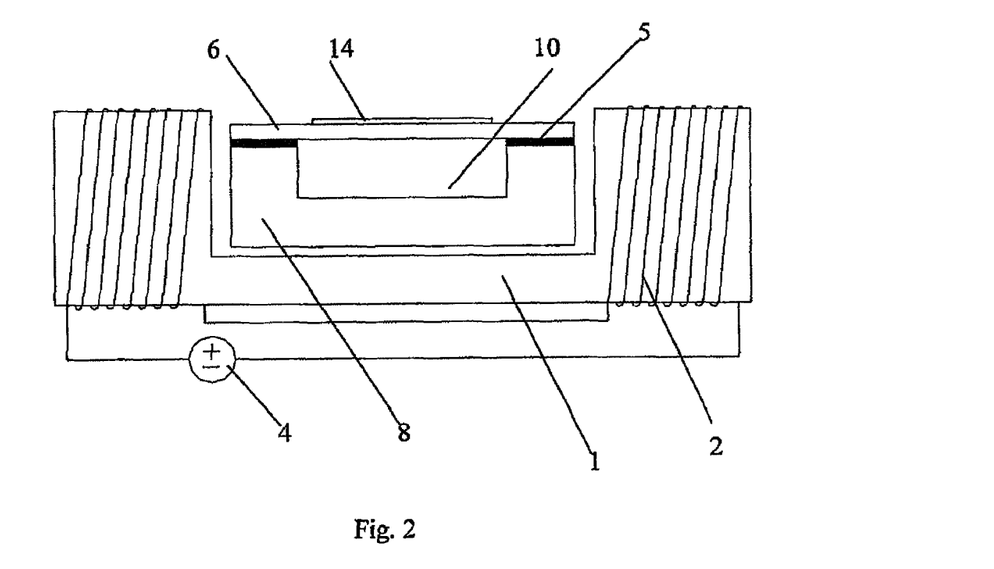
FIG. 2 is a structural diagram of electromagnetic ultrasonic transducer of the embodiment 2 of the present invention.
Figure 3:
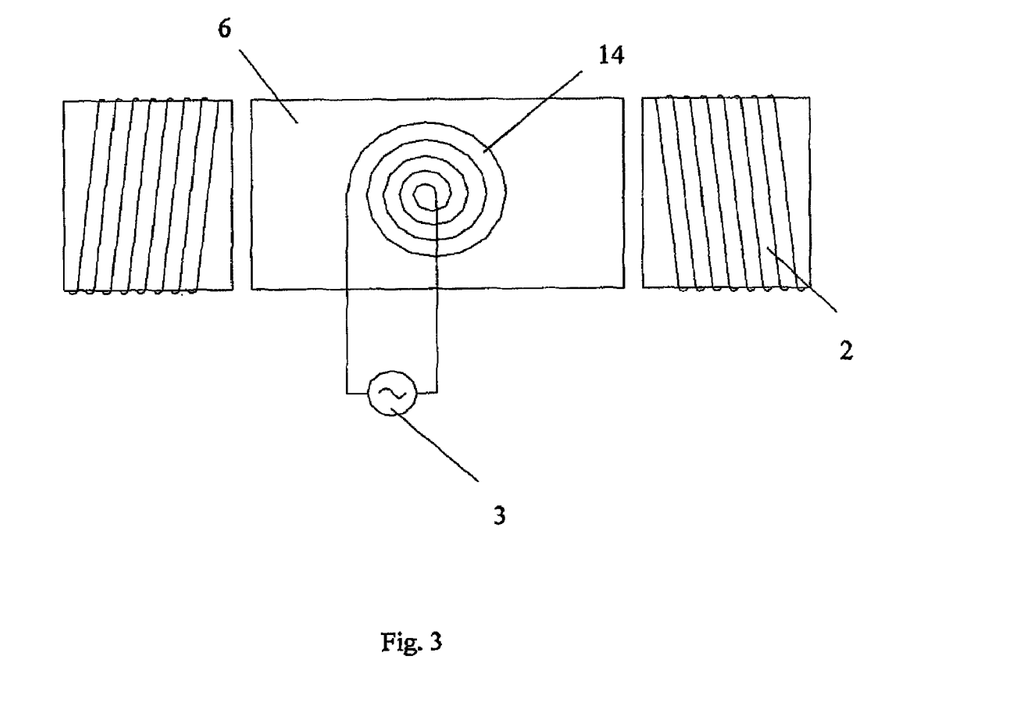
FIG. 3 is a top view of FIG. 2.

As shown in FIG. 2 and FIG. 3, the electromagnetic ultrasonic transducer comprises: an elastic board 6 disposed on the support 8, a magnetizer on the elastic board 6 and a magnet field generator for making the magnetizer vibrate.

Wherein, the magnetizer is of the order of microns. As shown in FIG. 3, the magnetizer is the coil lithographed by micromachining technology (for example, photolithographic way) on the elastic board 6, i.e. the photolithographic coil 14, which is connected to A. C. power supply 3. In this embodiment, the thickness of photolithographic coil 14 ranges from 0.5 to 200 microns.

The magnet field generator comprises: a concave soft magnet 1, coil 2 wound around two protuberant parts of the concave soft magnet 1 and D. C. power supply 4 connected to the coil 2. Wherein, the support 8 is fixed at the concave in the middle of concave soft magnet 1 and adopts non-magnetizable material.

The elastic board 6 is rectangle-shaped. In this embodiment, the elastic board 6 is also of the order of microns with a length ranging from 10 to 300 microns, a width ranging from 10 to 300 microns and a thickness ranging from 5 to 500 microns.

The support 8 is a concave one also. Two protuberant parts of the support 8 are connected to the elastic board 6 by elastic fixing material 5.

After the support 8 is connected to the elastic board 6, an air sink 10 is formed. In this embodiment, the length of the air sink ranges from 10 to 200 microns, the width from 10 to 200 microns and the thickness from 10 to 50 microns.

In this embodiment, the coil 2 winds around two protuberant parts of the concave soft magnet 1. The soft magnet 1 with this winding way generates magnetic force in a direction that the direction of magnetic field generated by soft magnet 1 is vertical to the direction of magnetic field generated in the photolithographic coil 14. The direction of this magnetic force can make the elastic board 6 vibrate with a maximum intensity and accordingly the intensity of ultrasonic waves produced is also the maximum. Therefore, in this embodiment, it is a preferable embodiment that the coil 2 winds around two protuberant parts of the concave soft magnet 1.

Other structures in this embodiment are the same as those in the embodiment 1.

When this electromagnetic ultrasonic transducer is used, the D. C. power supply 4 provides D. C. power to the coil 2. Because the coil 2 winds around the soft magnet 1, the soft magnet 1 is magnetized. Meanwhile, the A. C. power supply provides A. C. power to the photolithographic coil 14. Because the photolithographic coil 14 is located on the surface of the elastic board 6, the elastic board 6 is magnetized. Thus, under the action of A. C. power supply, the photolithographic coil 14 generates magnetic field force in the magnetic field of the coil 2 (the frequency of this force shall be kept consistent with the frequency of the A. C. power supply added to the photolithographic coil 14 and the force is in direct ratio with the current). Because the soft magnet 1 is fixed and the elastic board 6 is movable, the elastic board 6 vibrates and generates the ultrasonic waves under the action of A. C. power supply.

Embodiment 3

Figure 4:
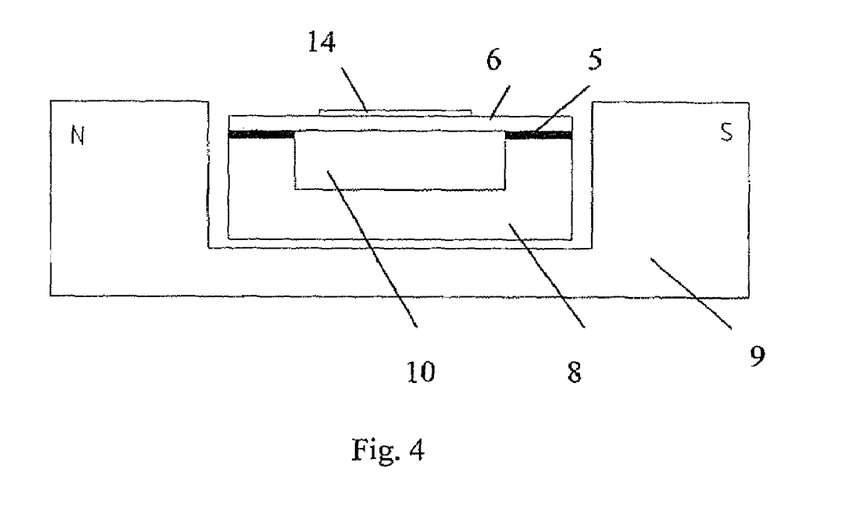
FIG. 4 is a structural diagram of electromagnetic ultrasonic transducer of the embodiment 3 of the present invention.
Figure 5:
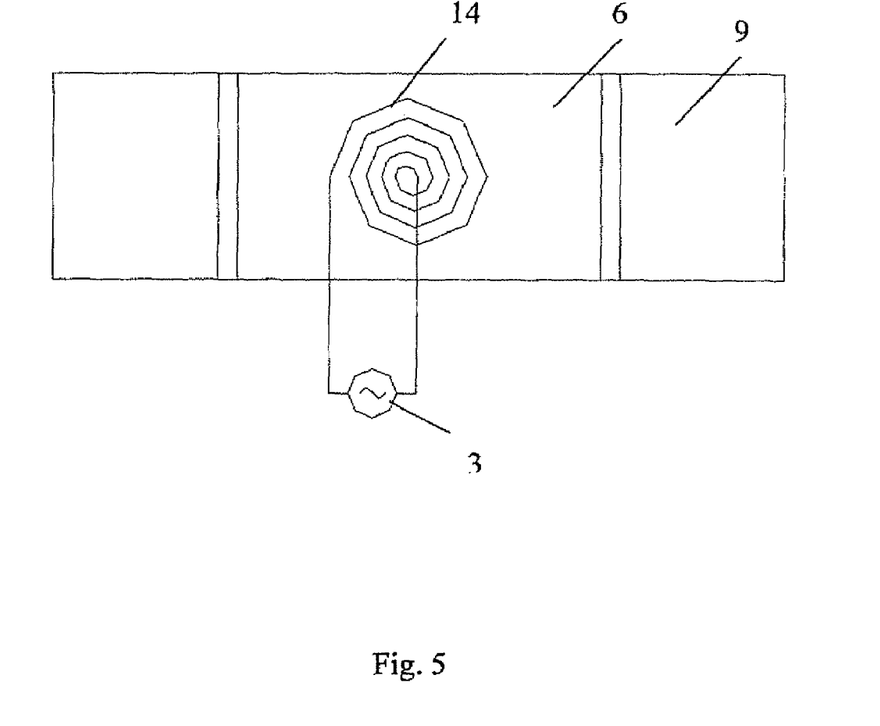
FIG. 5 is a top view of FIG. 4.

As shown in FIG. 4 and FIG. 5, the electromagnetic ultrasonic transducer of this embodiment is different from that in embodiment 2 because their magnet field generators are different. The concave permanent magnet 9 is used in this embodiment to replace the concave soft magnet 1, coil 2 wound around two protuberant parts of the concave soft magnet 1 and D. C. power supply 4 connected to the coil 2 in the embodiment 2.

Other structures and methods of use in this embodiment are the same as those in the embodiment 2.

Embodiment 4

Figure 6:
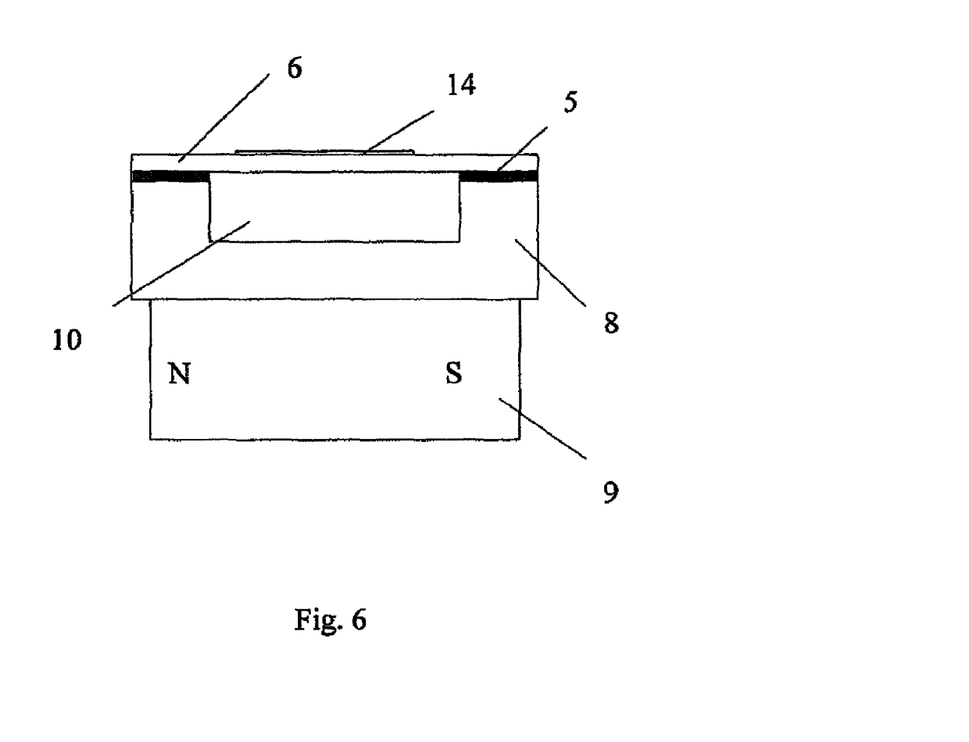
FIG. 6 is a structural diagram of electromagnetic ultrasonic transducer of the embodiment 4 of the present invention.
Figure 7:
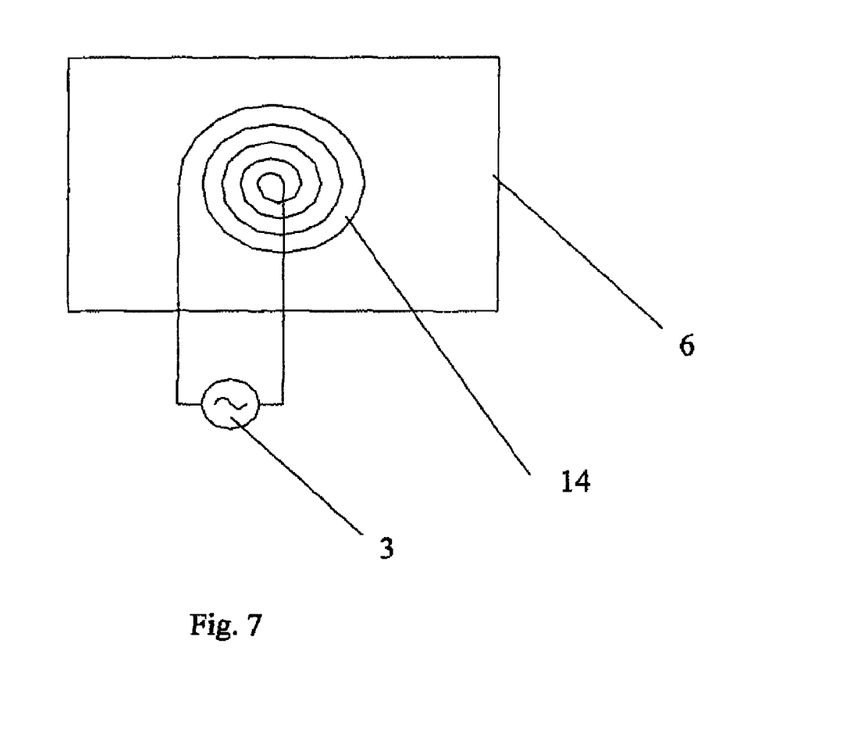
FIG. 7 is a top view of FIG. 6 and FIG. 8.

As shown in FIG. 6 and FIG. 7, the electromagnetic ultrasonic transducer of this embodiment comprises: an elastic board 6, a concave support 8 for supporting the elastic board and a permanent magnet 9, which is under the support 8 and connected to it by a fixed joint. The support 8 and the elastic board 6 are jointed by elastic fixing material 5. There is a photolithographic coil 14 on the elastic board 6 and this coil is connected to A. C. power supply 3. The support 8 is a concave one. After the support 8 is connected to the elastic board 6, an air sink 10 is formed.

When this electromagnetic ultrasonic transducer is used, the A. C. power supply provides A. C. power to the photolithographic coil 14. Because the photolithographic coil 14 is located on the surface of the elastic board 6, the elastic board 6 is magnetized. Thus, under the action of A. C. power supply, the photolithographic coil 14 generates magnetic field force in the magnetic field of the permanent magnet 9 (the frequency of this force shall be kept consistent with the frequency of the A. C. power supply added to the photolithographic coil 14 and the force is in direct ratio with the current). Because the permanent magnet 9 is fixed and the elastic board 6 is movable, the elastic board 6 vibrates and generates the ultrasonic waves under the action of A. C. power supply.

In this embodiment, in order to make the elastic board 6 vibrate and generate ultrasonic waves with maximum intensity, the preferable fixing way for magnetic poles of the permanent magnet 9 is shown in FIG. 7, i.e. the installation direction of the permanent magnet 9 is the direction that the direction of magnetic field generated by the permanent magnet is vertical to the current direction of the photolithographic coil 14 on the elastic board 6.

Other structures and methods of use in this embodiment are the same as those in the embodiment 1.

Embodiment 5

Figure 8:
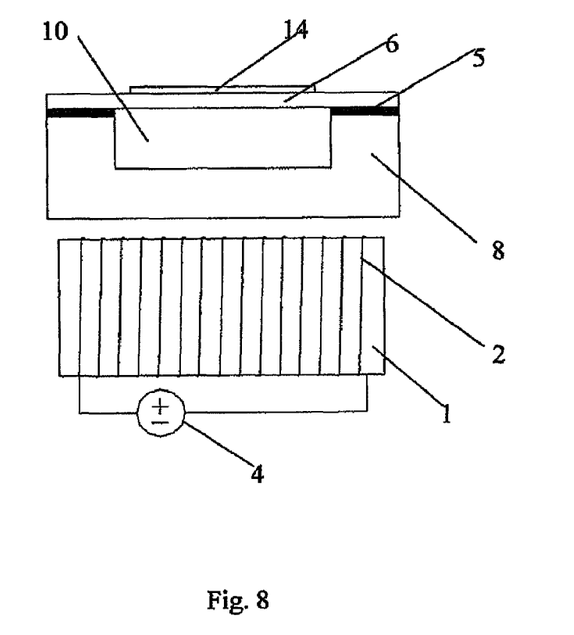
FIG. 8 is a structural diagram of electromagnetic ultrasonic transducer of the embodiment 5 of the present invention.

As shown in FIG. 7 and FIG. 8, the electromagnetic ultrasonic transducer of this embodiment is different from that in embodiment 4 because their magnet field generators are different. In this embodiment, the soft magnet 1, the coil 2 wound around soft magnet 1 and D. C. power supply 4 connected to the coil 2 are used to replace the permanent magnet 9 in embodiment 4.

When this electromagnetic ultrasonic transducer is used, the D. C. power supply 4 provides D. C. power to the coil 2. Because the coil 2 winds around the soft magnet 1, the soft magnet 1 is magnetized. Under the action of A. C. power supply provided to the photolithographic coil 14, the photolithographic coil 14 generates magnetic field force in the magnetic field of the coil 2 (the frequency of this force shall be kept consistent with the frequency of the A. C. power supply added to the photolithographic coil 14 and the force is in direct ratio with the current). Because the soft magnet 1 is fixed and the elastic board 6 is movable, the elastic board 6 vibrates and generates the ultrasonic waves under the action of A. C. power supply.

In this embodiment, in order to make the elastic board 6 vibrate and generate ultrasonic waves with maximum intensity, the preferable way of winding around the soft magnet 1 of the coil 2 is shown in FIG. 8, i.e. the magnetic field generated by coil 2 wound spirally is vertical to the current direction of the photolithographic coil 14 on the elastic board 6.

Other structures and methods of use in this embodiment are the same as those in the embodiment 4.

The embodiments 1 to 5 mainly describe the single electromagnetic ultrasonic transducer. The following embodiments 6 to 9 mainly describe the electromagnetic ultrasonic transducers array, which are integrated by multiple single electromagnetic ultrasonic transducers. The electromagnetic ultrasonic transducers array can be used to make different ultrasonic therapeutic applicator for treatment of different kinds of diseases, for example, a self-focusing ultrasonic therapeutic applicator suitable for treatment of liver tumor can be made.

Embodiment 6

Figure 9:
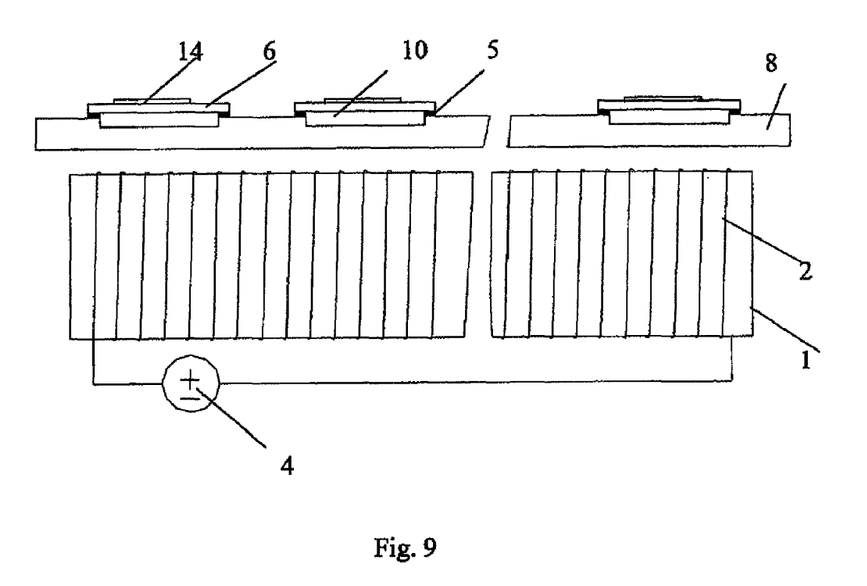
FIG. 9 is a structural diagram of electromagnetic ultrasonic transducers array of the embodiment 6 of the present invention.
Figure 10:
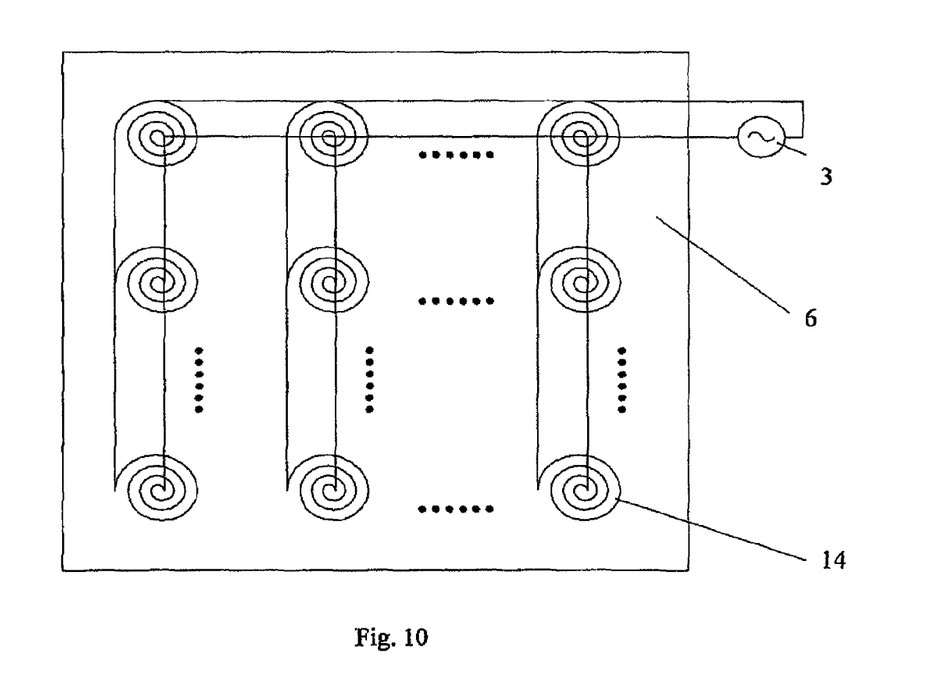
FIG. 10 is a top view of FIG. 9, FIG. 11 and FIG. 12.

As shown in FIG. 9 and FIG. 10, the electromagnetic ultrasonic transducers array of this present embodiment comprises: the soft magnet 1, the support 8 fixed on the soft magnet 1 with multiple concave openings and multiple elastic boards 6. There is a photolithographic coil 14 on each elastic board 6. Multiple photolithographic coils 14 are connected to each other in parallel and then connected to an A. C. power supply.

Wherein, both the elastic board 6 and the photolithographic coil 14 on it are of the order of microns. In this embodiment, the elastic board 6 is a rectangle-shaped board with a length ranging from 10 to 300 microns, a width ranging from 10 to 300 microns and a thickness ranging from 5 to 500 microns. The cord diameter of the photolithographic coil 14 ranges from 0.5 to 100 microns and its thickness ranges from 0.5 to 200 microns.

All elastic boards 6 are fixed respectively on the multiple concave openings of the support 8 with elastic fixing material and then air sinks 10 are formed. In this embodiment, the length of the air sink ranges from 10 to 200 microns, the width from 10 to 200 microns and the thickness from 10 to 50 microns.

The coil 2 winds around the soft magnet 1 and is connected to D. C. power supply 4.

Wherein, the elastic boards 6 are arranged on the support 8 in any forms or any regular arrangements also.

When this electromagnetic ultrasonic transducers array is used, the D. C. power supply 4 provides D. C. power to the coil 2. Because the coil 2 winds around the soft magnet 1, the soft magnet 1 is magnetized. Under the action of A. C. power supply provided to the photolithographic coil 14, the photolithographic coil 14 generates magnetic field force in the magnetic field of the coil 2 (the frequency of this force shall be kept consistent with the frequency of the A. C. power supply added to the photolithographic coil 14 and the force is in direct ratio with the current). Because the soft magnet 1 is fixed and the elastic board 6 is movable, the elastic board 6 vibrates and generates the ultrasonic waves under the action of A. C. power supply.

In this embodiment, in order to make the elastic board 6 vibrate and generate ultrasonic waves with maximum intensity, the preferable way of winding around the soft magnet 1 of the coil 2 is shown in FIG. 9, i.e. the magnetic field generated by coil 2 wound spirally is vertical to the current direction of the photolithographic coil 14 on the elastic board 6

Embodiment 7

Figure 11:
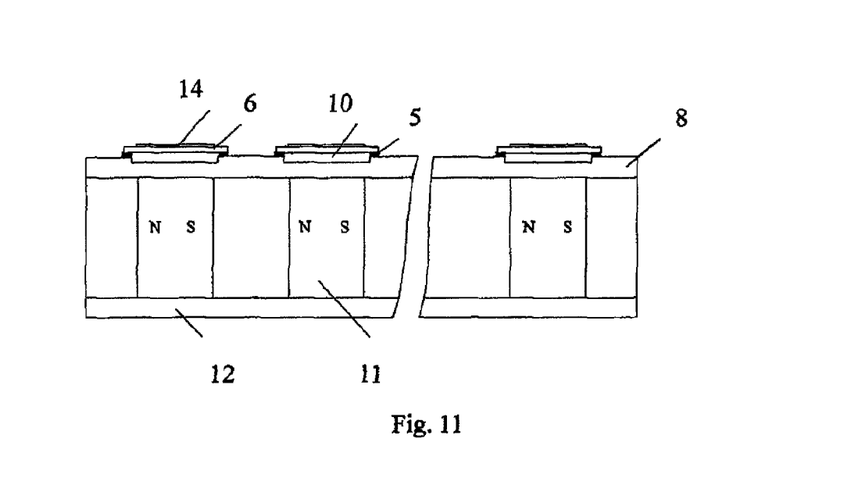
FIG. 11 is a structural diagram of electromagnetic ultrasonic transducers array of the embodiment 7 of the present invention.

As shown in FIG. 10 and FIG. 11, the electromagnetic ultrasonic transducers array of this present embodiment comprises: the comb permanent magnet 11, the fixing for comb permanent magnet 12, the supports 8 fixed on the comb permanent magnet 11 with multiple concave openings and the elastic boards 6. There is a photolithographic coil 14 on each elastic board 6. Multiple photolithographic coils 14 are connected to each other in parallel and then connected to an A. C. power supply 3.

Wherein, both the elastic board 6 and the photolithographic coil 14 on it are of the order of microns. In this embodiment, the elastic board 6 is a rectangle-shaped board with a length ranging from 10 to 300 microns, a width ranging from 10 to 300 microns and a thickness ranging from 5 to 500 microns. The cord diameter of the photolithographic coil 14 ranges from 0.5 to 100 microns and its thickness ranges from 0.5 to 200 microns.

All elastic boards 6 are fixed respectively on the multiple concave openings of the support 8 with elastic fixing material 5 and then air sinks 10 are formed. In this embodiment, the length of the air sink ranges from 10 to 200 microns, the width from 10 to 200 microns and the thickness from 10 to 50 microns.

When this electromagnetic ultrasonic transducer is used, the A. C. power supply provides A. C. power to the photolithographic coil 14. Because the photolithographic coil 14 is located on the surface of the elastic board 6, the elastic board 6 is magnetized. Thus, under the action of A. C. power supply, the photolithographic coil 14 generates magnetic field force in the magnetic field of the comb permanent magnet 11 (the frequency of this force shall be kept consistent with the frequency of the A. C. power supply added to the photolithographic coil 14 and the force is in direct ratio with the current). Because the comb permanent magnet 11 is fixed and the elastic board 6 is movable, the elastic board 6 vibrates and generates the ultrasonic waves under the action of A. C. power supply.

In this embodiment, in order to make the elastic board 6 vibrate and generate ultrasonic waves with maximum intensity, the preferable fixing way for magnetic poles of each unit of the comb permanent magnet 11 is shown in FIG. 11, i.e. the installation direction of the permanent magnet 11 is the direction that the direction of magnetic field generated by the permanent magnet is vertical to the current direction of the photolithographic coil 14 on the elastic board 6.

Embodiment 8

Figure 12:
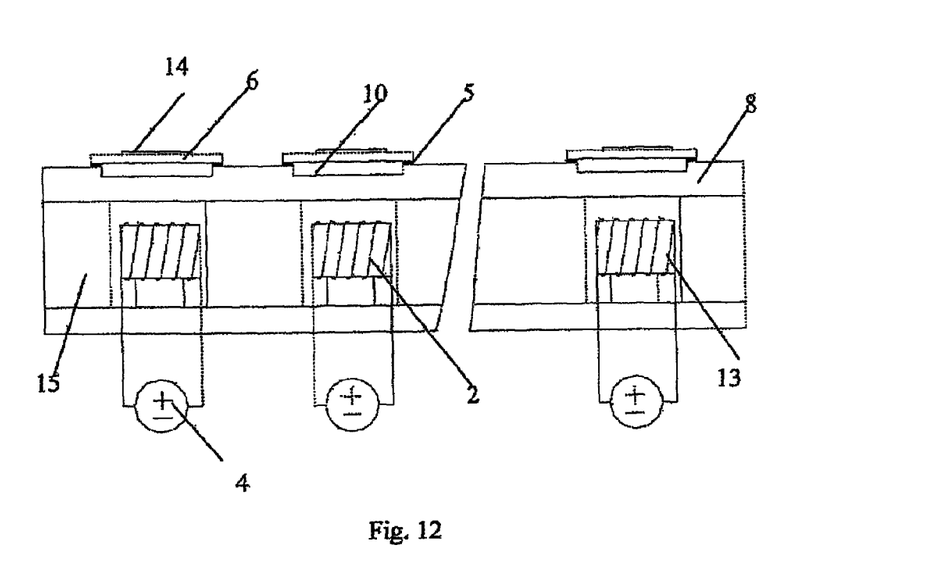
FIG. 12 is a structural diagram of electromagnetic ultrasonic transducers array of the embodiment 8 of the present invention.

As shown in FIG. 10 and FIG. 12, the electromagnetic ultrasonic transducers array of this present embodiment comprises: the comb soft magnet 13, the fixing for comb soft magnet 15, the supports 8 fixed on the comb soft magnet 13 with multiple concave openings and the elastic boards 6. There is a photolithographic coil 14 on each elastic board 6. Multiple photolithographic coils 14 are connected to each other in parallel and then connected to an A. C. power supply 3. On the fixing for comb soft magnet 15, there are holes to hold multiple comb soft magnet units. Each comb soft magnet unit is wound by the coil 2 and each coil 2 is connected to a D. C. power supply 4.

Wherein, both the elastic board 6 and the photolithographic coil 14 on it are of the order of microns. In this embodiment, the elastic board 6 is a rectangle-shaped plate with a length ranging from 10 to 300 microns, a width ranging from 10 to 300 microns and a thickness ranging from 5 to 500 microns. The cord diameter of the photolithographic coil 14 ranges from 0.5 to 100 microns and its thickness ranges from 0.5 to 200 microns.

A plurality of elastic boards 6 are fixed respectively on the multiple concave openings of the support 8 with elastic fixing material 5 and then air sinks 10 are formed. In this embodiment, the length of the air sink ranges from 10 to 200 microns, the width from 10 to 200 microns and the thickness from 10 to 50 microns.

When this electromagnetic ultrasonic transducer is used, the D. C. power supply 4 provides D. C. power to the coil 2. Because the coil 2 winds around the each comb soft magnet unit, the comb soft magnet unit is magnetized when it is energized. The A. C. power supply provides A. C. power to the photolithographic coil 14. Because the photolithographic coil 14 is fixed on the surface of the elastic board 6, the elastic board 6 is magnetized. Thus, under the action of A. C. power supply, the photolithographic coil 14 produces magnetic field force in the magnetic field of the coil 2 (the frequency of this force shall be kept consistent with the frequency of the A. C. power supply added to the photolithographic coil 14 and the force is in direct ratio with the current). Because the soft magnet 1 is fixed and the elastic board 6 is movable, the elastic board 6 vibrates and generates the ultrasonic waves under the action of A. C. power supply.

It shall be noted that when the electromagnetic ultrasonic transducers array in this embodiment is used, some comb soft magnet units selected are energized according to the needs, while not always all comb soft magnet units are energized at the same time.

In this embodiment, in order to make the elastic board 6 vibrate and generate ultrasonic waves with maximum intensity, the preferable way of winding around each unit of the comb soft magnet 13 of the coil 2 is shown in FIG. 12, i.e. the direction of magnetic field generated by coil 2 wound spirally is vertical to the current direction of the coil on the elastic board 6.

Embodiment 9

Figure 13:
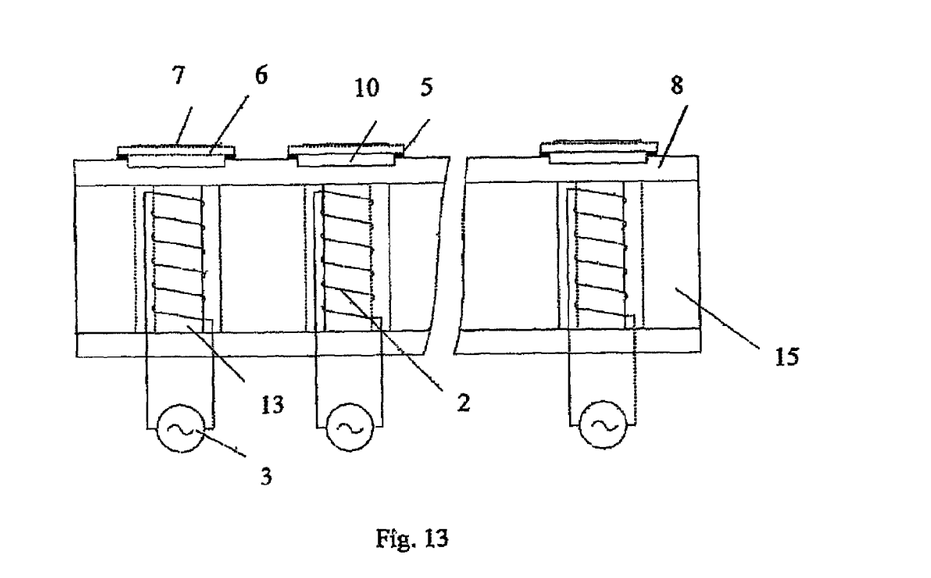
FIG. 13 is a structural diagram of electromagnetic ultrasonic transducers array of the embodiment 9 of the present invention.
Figure 14:
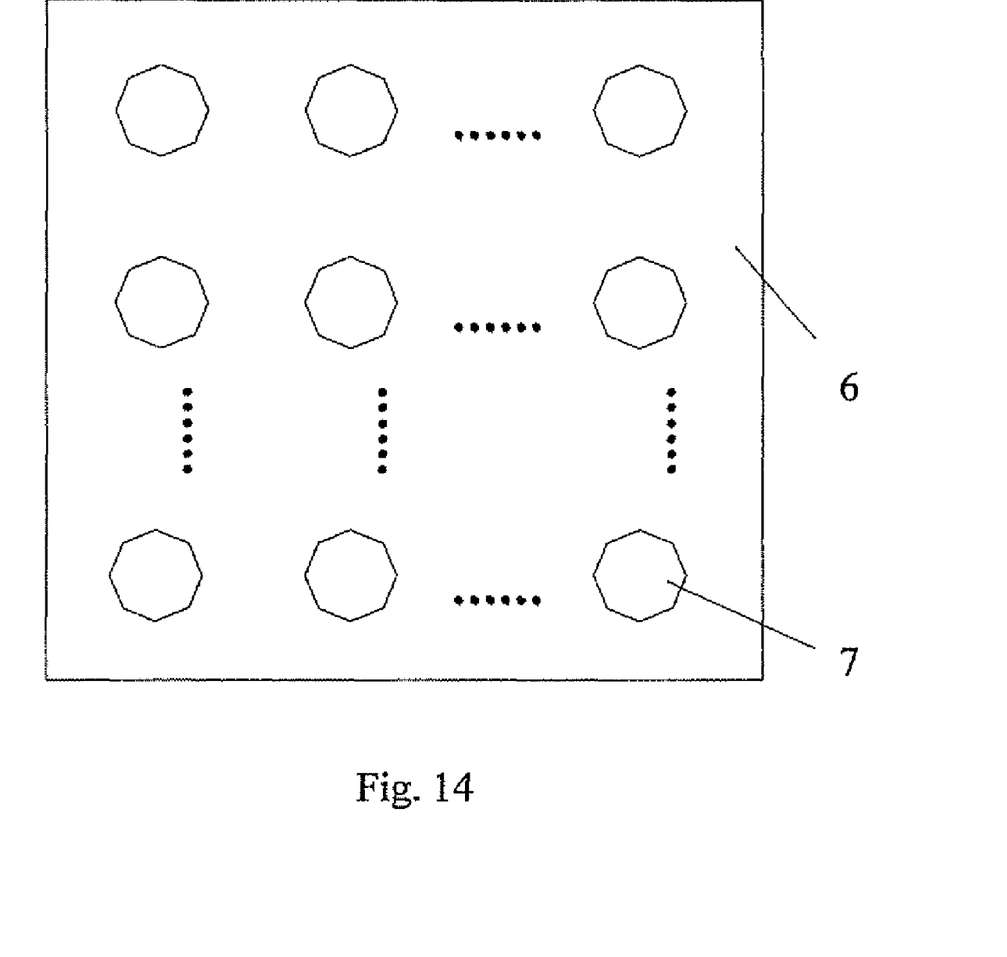
FIG. 14 is a top view of FIG. 13.

As shown in FIG. 13 and FIG. 14, the difference between this embodiment and the embodiment 7 is that the comb soft magnet 13, the coil 2 wound around each comb soft magnet unit and the A. C. power supply 3 connected to the coil 2 are used in this embodiment to replace comb permanent magnet 11 in the embodiment 7 and the magnet conducting diaphragm 7 plated on the elastic board 6 is used in this embodiment to replace the photolithographic coil 14 and the A. C. power supply connected to it in the embodiment 7.

The magnetizer on the elastic board in this embodiment adopts magnet conducting diaphragm 7 with a thickness ranging from 1 to 300 microns. The magnet conducting diaphragm 7 is magnetized repeatedly in the magnetic field and meanwhile a force is generated and then a vibration is generated accordingly.

In this embodiment, in order to make the elastic board 6 vibrate and generate ultrasonic waves with maximum intensity, the preferable way of winding around each unit of the comb soft magnet 13 of the coil 2 is shown in FIG. 13, i.e. the coil 2 wound spirally generates the maximum magnetic field intensity where the magnet conducting diaphragm 7 is located. Therefore the magnet conducting diaphragm 7 gains the maximum vibration.

Other structures and methods of use in this embodiment are the same as those in the embodiment 7.

The invention claimed is:

1. An electromagnetic ultrasonic transducer comprising a support, an elastic board disposed on the support, a magnetizer on the elastic board, and a magnet field generator for making the magnetizer vibrate, wherein the thickness of the magnetizer is of the order of microns, the magnetizer is an elastic coil which is configured as a photolithographic coil manufactured by use of semiconductor photolithography and chemical corrosion technology; the support is made of a non-magnetizable material; the magnet field generator is configured as a soft magnet wound by coils, and the coils are connected to a D.C. power supply; the shape of the soft magnet is concave, and the support is fixed at the concave in the middle of the soft magnet; the coils are wound around two protuberant parts at ends of the soft magnet; the photolithographic coil is connected to an A.C. power supply.

2. The electromagnetic ultrasonic transducer of claim 1, wherein a diameter of the elastic coil ranges from 0.5 to 100 microns and the thickness ranges from 0.5 to 200 microns.

3. The electromagnetic ultrasonic transducer as claimed in claim 1, wherein the frequency of the magnetic field force, which is generated by the photolithographic coil, is equal to the frequency of the alternating current in the photolithographic coil and this magnetic field force is in direct ratio with this alternating current.

4. The electromagnetic ultrasonic transducer as claimed in claim 1, wherein the shape of said support is concave, and two ends of the elastic board are fixed on two protuberant parts at both ends of the support by an elastic fixing material; thus, forming an air sink at the concave in the middle of the support, and wherein the length of said air sink ranges from 10 to 200 microns, the width from 10 to 200 microns and the thickness from 10 to 50 microns.

5. The electromagnetic ultrasonic transducer of claim 1, wherein a thickness of said elastic board is of the order of microns; wherein when the elastic board is rectangle-shaped, its length and width range from 10 to 1000 microns and its thickness ranges from 5 to 500 microns; when the elastic board is round-shaped, its diameter ranges from 10 to 1000 microns and its thickness ranges from 5 to 500 microns.

6. An electromagnetic ultrasonic transducer comprising a support, an elastic board disposed on the support, a magnetizer on the elastic board, and a magnet field generator for making the magnetizer vibrate, wherein the thickness of the magnetizer is of the order of microns, the magnetizer is an elastic coil which is configured as a photolithographic coil manufactured by use of semiconductor photolithography and chemical corrosion technology; the support is made of a non-magnetizable material; the magnet field generator is configured as a permanent magnet; the permanent magnet is concave-shaped and the support is fixed at the concave in the middle of the permanent magnet; the photolithographic coil is connected to an A.C. power supply.

7. The electromagnetic ultrasonic transducer as claimed in claim 6, wherein the frequency of the magnetic field force, which is generated by the photolithographic coil, is equal to the frequency of the alternating current in the photolithographic coil and this magnetic field force is in direct ratio with this alternating current.

8. The electromagnetic ultrasonic transducer as claimed in claim 6, wherein the shape of said support is concave, and two ends of the elastic board are fixed on two protuberant parts at both ends of the support by an elastic fixing material; thus, forming an air sink at the concave in the middle of the support, and wherein the length of said air sink ranges from 10 to 200 microns, the width from 10 to 200 microns and the thickness from 10 to 50 microns.

9. The electromagnetic ultrasonic transducer of claim 6, wherein a diameter of the elastic coil ranges from 0.5 to 100 microns and the thickness ranges from 0.5 to 200 microns.

10. An electromagnetic ultrasonic transducer comprising a support, an elastic board disposed on the support, a magnetizer on the elastic board, and a magnet field generator for making the magnetizer vibrate, wherein the thickness of the magnetizer is of the order of microns, the magnetizer is an elastic coil which is configured as a photolithographic coil manufactured by use of semiconductor photolithography and chemical corrosion technology; the support is made of a non-magnetizable material; the magnet field generator is configured as a permanent magnet; the support is placed on the permanent magnet and is fixed and connected to it; the photolithographic coil is connected to an A.C. power supply.

11. An electromagnetic ultrasonic transducers array, comprising multiple electromagnetic ultrasonic transducers as claimed in claim 10; wherein the thickness of the elastic board in each ultrasonic transducer is of the order of microns; all the supports of these transducers are integrated; and all their photolithographic coils are connected to each other in parallel and then connected to an A.C. power supply.

12. The electromagnetic ultrasonic transducers array as claimed in claim 11, wherein the frequency of the magnetic field force, which is generated by the photolithographic coil in the magnet field generators, is equal to the frequency of the alternating current in the photolithographic coil and this magnetic field force is in direct ratio with this alternating current.

13. The electromagnetic ultrasonic transducers array as claimed in claim 11, wherein there are multiple concave openings on said support, and two ends of the elastic board in each transducer are fixed respectively on both ends of the multiple concave openings of the support with elastic fixing material and then air sinks are formed within the concave openings.

14. The electromagnetic ultrasonic transducer as claimed in claim 10, wherein the frequency of the magnetic field force, which is generated by the photolithographic coil, is equal to the frequency of the alternating current in the photolithographic coil and this magnetic field force is in direct ratio with this alternating current.

15. The electromagnetic ultrasonic transducer as claimed in claim 10, wherein the shape of said support is concave, and two ends of the elastic board are fixed on two protuberant parts at both ends of the support by an elastic fixing material; thus, forming an air sink at the concave in the middle of the support, and wherein the length of said air sink ranges from 10 to 200 microns, the width from 10 to 200 microns and the thickness from 10 to 50 microns.

16. The electromagnetic ultrasonic transducer of claim 10, wherein a diameter of the elastic coil ranges from 0.5 to 100 microns and the thickness ranges from 0.5 to 200 microns.

17. An electromagnetic ultrasonic transducer comprising a support, an elastic board disposed on the support, a magnetizer on the elastic board, and a magnet field generator for making the magnetizer vibrate, wherein the thickness of the magnetizer is of the order of microns, the magnetizer is an elastic coil which is configured as a photolithographic coil manufactured by use of semiconductor photolithography and chemical corrosion technology; the support is made of a non-magnetizable material; the magnet field generator is disposed under the support and is configured as a soft magnet wound by coils; the coils are connected to a D.C. power supply; the photolithographic coil is connected to an A.C. power supply.

18. The electromagnetic ultrasonic transducer of claim 17, wherein the winding direction of the coils on the soft magnet makes the direction of current in the photolithographic coils be vertical to the direction of magnetic field in the soft magnet.

19. An electromagnetic ultrasonic transducers array, comprising multiple electromagnetic ultrasonic transducers as claimed in claim 17; wherein all the supports of these transducers are integrated; all their magnet field generators are integrated and are connected to a D.C. power supply; and all their photolithographic coils are connected to each other in parallel and then connected to an A.C. power supply.

20. The electromagnetic ultrasonic transducers array of claim 19, wherein the winding direction of the coil around the soft magnet makes the direction of current in the photolithographic coils be vertical to the direction of magnetic field in the soft magnet.

21. The electromagnetic ultrasonic transducers array as claimed in claim 19, wherein the frequency of the magnetic field force, which is generated by the photolithographic coil in the magnet field generators, is equal to the frequency of the alternating current in the photolithographic coil and this magnetic field force is in direct ratio with this alternating current.

22. The electromagnetic ultrasonic transducers array as claimed in claim 19, wherein there are multiple concave openings on said support, and two ends of the elastic board in each transducer are fixed respectively on both ends of the multiple concave openings of the support with elastic fixing material and then air sinks are formed within the concave openings.

23. The electromagnetic ultrasonic transducers array of claim 22, wherein the length of said air sink ranges from 10 to 200 microns, the width from 10 to 200 microns and the thickness from 10 to 50 microns.

24. An electromagnetic ultrasonic transducers array, comprising multiple electromagnetic ultrasonic transducers as claimed in claim 17; wherein the thickness of the elastic board in each ultrasonic transducer is of the order of microns; all the supports of these transducers are integrated; the soft magnets wound by coils are respectively fixed under every elastic board; and all their photolithographic coils are connected to each other in parallel and then connected to an A.C. power supply.

25. The electromagnetic ultrasonic transducers array of claim 24, wherein the winding direction of the coil around the soft magnet makes the direction of current in the photolithographic coils be vertical to the direction of magnetic field in the soft magnet.

26. The electromagnetic ultrasonic transducers array as claimed in claim 24, wherein the frequency of the magnetic field force, which is generated by the photolithographic coil in the magnet field generators, is equal to the frequency of the alternating current in the photolithographic coil and this magnetic field force is in direct ratio with this alternating current.

27. The electromagnetic ultrasonic transducers array as claimed in claim 24, wherein there are multiple concave openings on said support, and two ends of the elastic board in each transducer are fixed respectively on both ends of the multiple concave openings of the support with elastic fixing material and then air sinks are formed within the concave openings.

28. The electromagnetic ultrasonic transducer as claimed in claim 17, wherein the frequency of the magnetic field force, which is generated by the photolithographic coil, is equal to the frequency of the alternating current in the photolithographic coil and this magnetic field force is in direct ratio with this alternating current.

29. The electromagnetic ultrasonic transducer as claimed in claim 17, wherein the shape of said support is concave, and two ends of the elastic board are fixed on two protuberant parts at both ends of the support by an elastic fixing material; thus, forming an air sink at the concave in the middle of the support, and wherein the length of said air sink ranges from 10 to 200 microns, the width from 10 to 200 microns and the thickness from 10 to 50 microns.

30. The electromagnetic ultrasonic transducer of claim 17, wherein a diameter of the elastic coil ranges from 0.5 to 100 microns and the thickness ranges from 0.5 to 200 microns.

* * * * *